United States Patent
Chanpura et al.

(10) Patent No.: US 8,653,815 B2
(45) Date of Patent: Feb. 18, 2014

(54) METHOD FOR DETERMINING FORMATION PARTICLE SIZE DISTRIBUTION USING WELL LOGGING MEASUREMENTS

(75) Inventors: Rajesh A. Chanpura, Sugar Land, TX (US); Yi-Qiao Song, Newton Center, MA (US); Mehmet Parlar, Sugar Land, TX (US); Lukasz Zielinski, Somerville, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 720 days.

(21) Appl. No.: 12/795,868

(22) Filed: Jun. 8, 2010

(65) Prior Publication Data

US 2010/0315081 A1 Dec. 16, 2010

Related U.S. Application Data

(60) Provisional application No. 61/186,089, filed on Jun. 11, 2009, provisional application No. 61/297,581, filed on Jan. 22, 2010.

(51) Int. Cl.
*G01V 3/00* (2006.01)

(52) U.S. Cl.
USPC .......................................... 324/303

(58) Field of Classification Search
USPC .............................. 324/300–322
See application file for complete search history.

(56) References Cited

U.S. PATENT DOCUMENTS

| | | | |
|---|---|---|---|
| 5,497,087 | A | 3/1996 | Vinegar |
| 6,933,719 | B2 | 8/2005 | Thomann |
| 7,257,490 | B2 | 8/2007 | Georgi |
| 7,356,413 | B2 | 4/2008 | Georgi |
| 7,363,161 | B2 | 4/2008 | Georgi |
| 2008/0221800 | A1 | 9/2008 | Gladkikh |
| 2010/0258304 | A1 | 10/2010 | Hegeman |
| 2010/0315081 | A1 | 12/2010 | Chanpura et al. |
| 2013/0057277 | A1 | 3/2013 | Zilinski et al. |

OTHER PUBLICATIONS

Hirasaki, et al. Fluid-rock characterization and interactions in NMR well logging. Aug. 31, 2002, pp. 1-173.

Chanpura et al.—A Review of Screen Selection for Standalone Applications and a New Mathodology—SPE127931—Presented at SPE International Symposium and Exhibition, Lafayette, Louisiana, USA, Feb. 10-12, 2010, pp. 84-95.

Mondal et al.—Numerical Simulations of Sand-Screen Performance in Standalone Applications—SPE134326—Presented at the SPE Annual Technical Conference and Exhibition, Florence, Italy, Sep. 20-22, 2010, pp. 472-483.

Chanpura et al.—"Advancements in Screen Testing, Interpretation and Modeling for Standalone Screen Applications"—SPE143731—Prepared for presentation at the SPE European Formation Damage Conference held in Noordwijk, The Netherlands, Jun. 7-10, 2011, pp. 1-14.

(Continued)

*Primary Examiner* — Dixomara Vargas
(74) *Attorney, Agent, or Firm* — David G. Matthews; Brandon S. Clark; Richard A. Fagin

(57) ABSTRACT

A method for determining particle size distribution of a subsurface rock formation using measurements of at least one nuclear magnetic resonance property made from within a wellbore penetrating the rock formation includes determining a distribution of nuclear magnetic relaxation times from the measurements of the at least one nuclear magnetic resonance property. A surface relaxivity of the formation is determined from measurements of a formation parameter. The relaxation time distribution and surface relaxivity are used to determine the particle size distribution.

26 Claims, 8 Drawing Sheets

(56) References Cited

OTHER PUBLICATIONS

Mondal et al.—"A New Method for the Design and Selection of Premium/Woven Sand Screens"—SPE146656—Prepared for presentation at the SPE Annual Technical Conference and Exhibition held in Denver, Colorado, USA, Oct. 30-Nov. 2, 2011.

Chanpura et al.—"Modeling of Square Mesh Screens in Slurry Test Conditions for Standalone Screen Applications"—SPE151637—Prepared for presentation at the SPE International Symposium and Exhibition on Formation Damage Control Held in Lafayette, Louisiana, U.S.A., Feb. 15-17, 2012.

J. Chen, Determination of Grain Size Distribution From NMR Relaxation Time Using Pore Scale Modeling, SCA2007-49; International Symposium of the Society of Core Analysists held in Calgary, Canada, Sep. 10-12, 2007.

M. Gladkikh, Method of Determining Formation Grain Size Distribution From Acoustic Velocities and NMR Relaxation Time Spectrum, SPWLA 49th Annual Logging Symposium, May 25-28, 2008.

D. L. Tiffin, New Criteria for Gravel and Screen Selection for Sand Control, SPE 39437 (1998).

Freed, et al., "Scaling Laws for Diffusion Coefficients in Mixtures of Alkanes", Physical Review Letters, vol. 94(6), Feb. 17, 2005, 4 pages.

Freed, Denise E., "Dependence on chain length of NMR relaxation times in mixtures of alkanes", Journal of Chemical Physics, vol. 126 (17), 2007, 10 pages.

International Search Report and Written Opinion of PCT/US2010/037969 dated Aug. 10, 2010.

METHOD FOR DETERMINING FORMATION PARTICLE SIZE DISTRIBUTION USING WELL LOGGING MEASUREMENTS

CROSS-REFERENCE TO RELATED APPLICATIONS

Priority is claimed from U.S. Provisional Application No. 61/186,089 filed on Jun. 11, 2009. Priority is also claimed from U.S. Provisional Application No. 61/297,581 filed on Jan. 22, 2010.

STATEMENT REGARDING FEDERALLY SPONSORED RESEARCH OR DEVELOPMENT

Not applicable.

BACKGROUND OF THE INVENTION

1. Field of the Invention

The invention relates generally to the field of subsurface formation evaluation using well logging measurements. More specifically, the invention relates to methods for determining particle size distribution of rock formations using nuclear magnetic resonance ("NMR") well logging measurements.

2. Background Art

Wellbores are drilled through subsurface rock formations for, among other purposes, extraction of useful fluids such as oil and gas from porous, permeable rock formations penetrated by such wellbores. The porous formations include rock mineral grains of various shapes and sizes, wherein the grains are bound to each other (cemented) in varying degrees depending on the post depositional history of the particular rock formation. The fluids are contained in the pore spaces. A wellbore is said to be "completed" when hydraulic connection is made between a formation that is intended to produce fluid and the Earth's surface using various conduits and flow control devices.

Particle size distribution (PSD) of rock formations, that is the distribution of sizes of the rock grains, is a physical parameter that is important for the selection of the completion type, sand screen type and opening size, and gravel size (if needed) of a "gravel pack" for control of formation solids when fluids are produced. PSD can be obtained from sieve analysis or laser particle size analysis of the rock formation from produced samples, bailed sample, side wall core or conventional core.

A sample of the rock formation can be easily obtained from a producing well in which a substantial volume of sand moves into the wellbore. However, the produced sand sample will generally have a higher percentage of fine-grained sand than what is originally present in the rock formation. This is because coarse sand particles tend to fall, rather than move upward to the surface, and settle at the bottom of the well when the sand moves into the wellbore. For the same reason, a bailed sample will generally have a higher fraction of coarse sand than what is present in the reservoir rock. Sand samples obtained from sidewall (percussion or drilled) cores can also give misleading results, particularly in the case of percussion sidewall cores. When the sample taking projectiles strike the face of the formation, they can crush the rock grains, generating more fine particles than may be present in the undisturbed rock formation. The sidewall core sample could also contain drilling fluid ("mud") solids that can be misidentified as formation material. The most representative formation sample is obtained from conventional (drilled) cores. However, such samples are not readily available in most cases due to cost of coring operations. If drilled core samples are available, small plugs can be taken out of the core at various longitudinal positions along such sample for a complete and accurate grain size distribution.

There is a need for other ways of obtaining particle size distribution of subsurface rock formations without the need to retrieve actual formation samples.

SUMMARY OF THE INVENTION

A method according to one aspect of the invention for determining particle size distribution of a subsurface rock formation using measurements of at least one nuclear magnetic resonance property made from within a wellbore penetrating the rock formation includes determining a distribution of nuclear magnetic relaxation times from the measurements of the at least one nuclear magnetic resonance property. A surface relaxivity of the formation is determined from measurements of a formation parameter. The relaxation time distribution and surface relaxivity are used to determine the particle size distribution.

A method for determining particle size distribution of a subsurface rock formation according to another aspect of the invention includes moving a nuclear magnetic resonance well logging instrument along a wellbore drilled through the subsurface rock formation. The instrument is used for measuring at least one nuclear magnetic resonance property of the rock formation. A distribution of nuclear magnetic relaxation times is determined from the measurements of the at least one nuclear magnetic resonance property. A surface relaxivity of the rock formation is determined from a measurement of a formation parameter. The relaxation time distribution and the surface relaxivity are used to determine the particle size distribution.

Other aspects and advantages of the invention will be apparent from the following description and the appended claims.

DETAILED DESCRIPTION

Figure 1A:
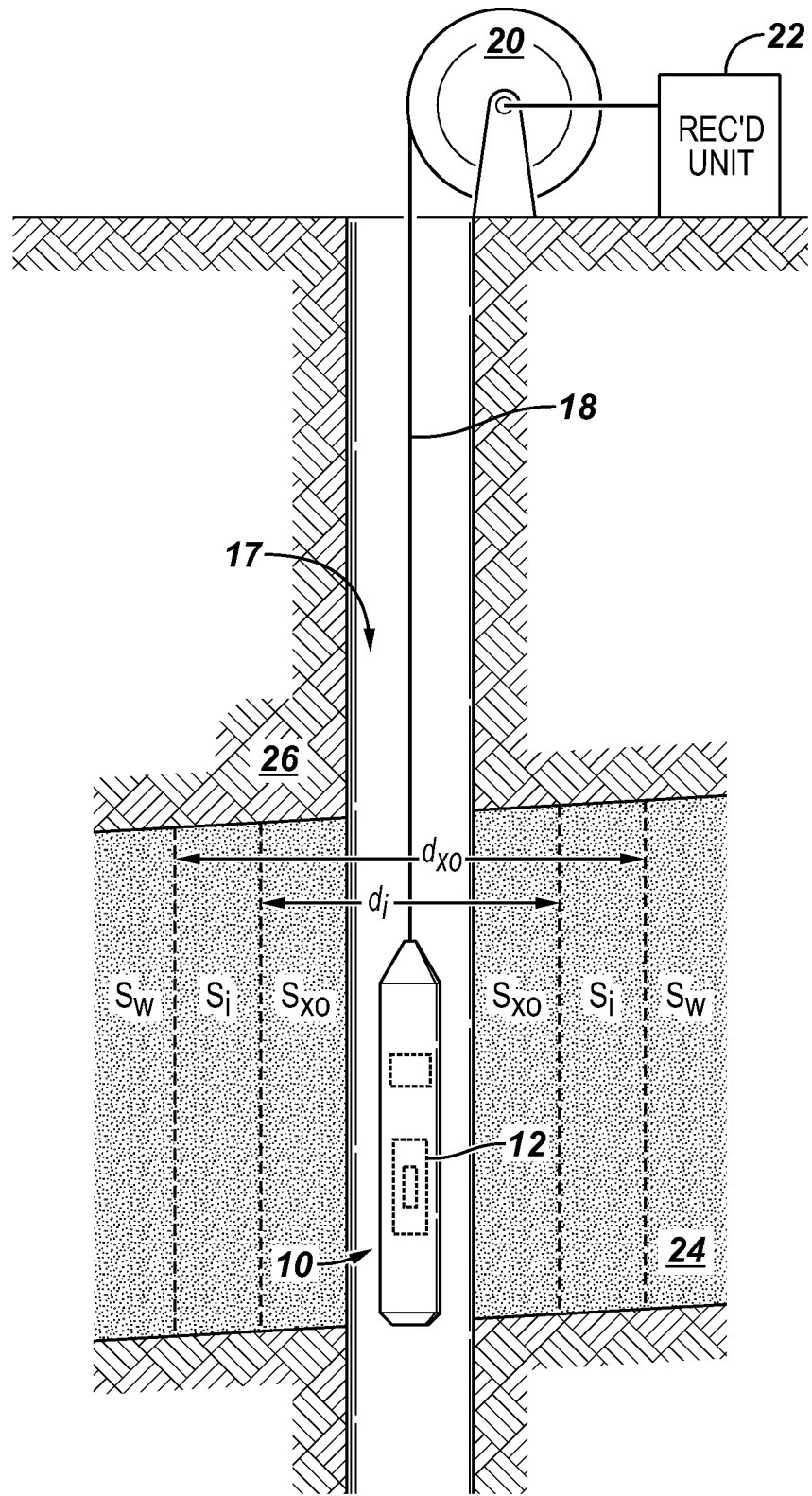
FIG. 1A shows a wireline NMR instrument deployed in a wellbore.

FIG. 1A shows an example nuclear magnetic resonance ("NMR") wireline well logging instrument 10 disposed in a wellbore 17 drilled through subsurface rock formations 26, 24. The instrument 10 is attached to one end of an armored electrical cable ("wireline") 18. The cable 18 may be extended into the wellbore 17 and withdrawn therefrom by a spooling device such as a winch 20 of types well known in the art. The cable 18 includes one or more insulated electrical conductors and, may include one or more optical fibers to communicate signals between the instrument 10 and a recording unit 22 disposed at the Earth's surface. The recording unit 22 may include a computer (not shown separately) having a screen or printer type data display, input controls and a data recording device for storage of signals (e.g., NMR measurements) communicated from the well logging instrument 10, as well as for storing or displaying calculated results made from NMR measurements made by the instrument 10.

The NMR instrument 10 includes a magnet 12 for inducing a static magnetic field in the formations 24, 26 having a predetermined spatial distribution of magnetic field amplitude. As the instrument 10 is moved along the interior of the wellbore 17, nuclei in the formations surrounding the wellbore are magnetically polarized along the direction of the magnet's 12 field. The instrument 10 also includes an antenna for inducing radio frequency ("RF") magnetic fields in the formations, and for detecting radio frequency signals induced by NMR phenomena excited in the formations by the static and RF magnetic fields. The particular portion of the formations adjacent to the wellbore from which the NMR signals originate depends on, among other factors, the spatial amplitude distribution of the static magnetic field and the RF frequency used to induce NMR phenomena in the formations. Some magnets may induce a region of substantially homogeneous field amplitude in a particular region in the formations; other types of magnets may induce static fields having a selected amplitude gradient in a particular region of interest. For certain types of measurements, e.g., diffusion, homogeneous field magnets may be supplemented by an electromagnet (not shown) configured to impart a selected magnitude gradient field superimposed on the static homogenous field.

Some formations, for example the one illustrated at 24 in FIG. 1A may be permeable and/or contain movable hydrocarbon in the pore spaces thereof. Proximate the wall of the wellbore 17, a portion of the formation 24 may be subjected to sufficient infiltration of the liquid phase of a fluid ("drilling mud"), called "mud filtrate", used to drill the wellbore 17, that substantially all of the mobile connate fluids in the pore spaces of the formation 24 are displaced by the mud filtrate. Depending on, for example, the fractional volume of pore space ("porosity") of the formation 24, and the filtrate characteristics of the drilling mud, the mud filtrate will fully displace all the mobile connate fluids to a depth represented by $d_{xo}$ in FIG. 1A. The foregoing is referred to as the diameter of the "flushed zone." Partial displacement of connate fluid is shown extending to a diameter represented by $d_i$, which is used to represent the diameter of the "invaded zone." At a certain lateral depth in the formation 24, beyond the diameter of the invaded zone, connate fluid is substantially undisturbed. A quantity of interest in determining possible fluid production in from the formation is the fractional volume of the pore space that is occupied by water (and its complement assumed to be occupied by hydrocarbons). In the uninvaded zone, such fractional volume, called "saturation", is represented by Sw. Invaded zone and flushed zone water saturations are represented, respectively, by Si and Sxo.

The example instrument shown in FIG. 1A is only for purposes of explaining the source of measurements that may be used with a method according to the invention and is not intended to limit the configurations of NMR well logging instrument that may be used to provide measurements for the method of the present invention. Further, reference to portions of formations that contain hydrocarbon are only for purposes of illustrating general principles of NMR well logging; as will be explained below, certain measurements of NMR properties may be made in formations known to be fully water saturated to simplify calculations of formation properties made from the NMR measurements.

Figure 1B:
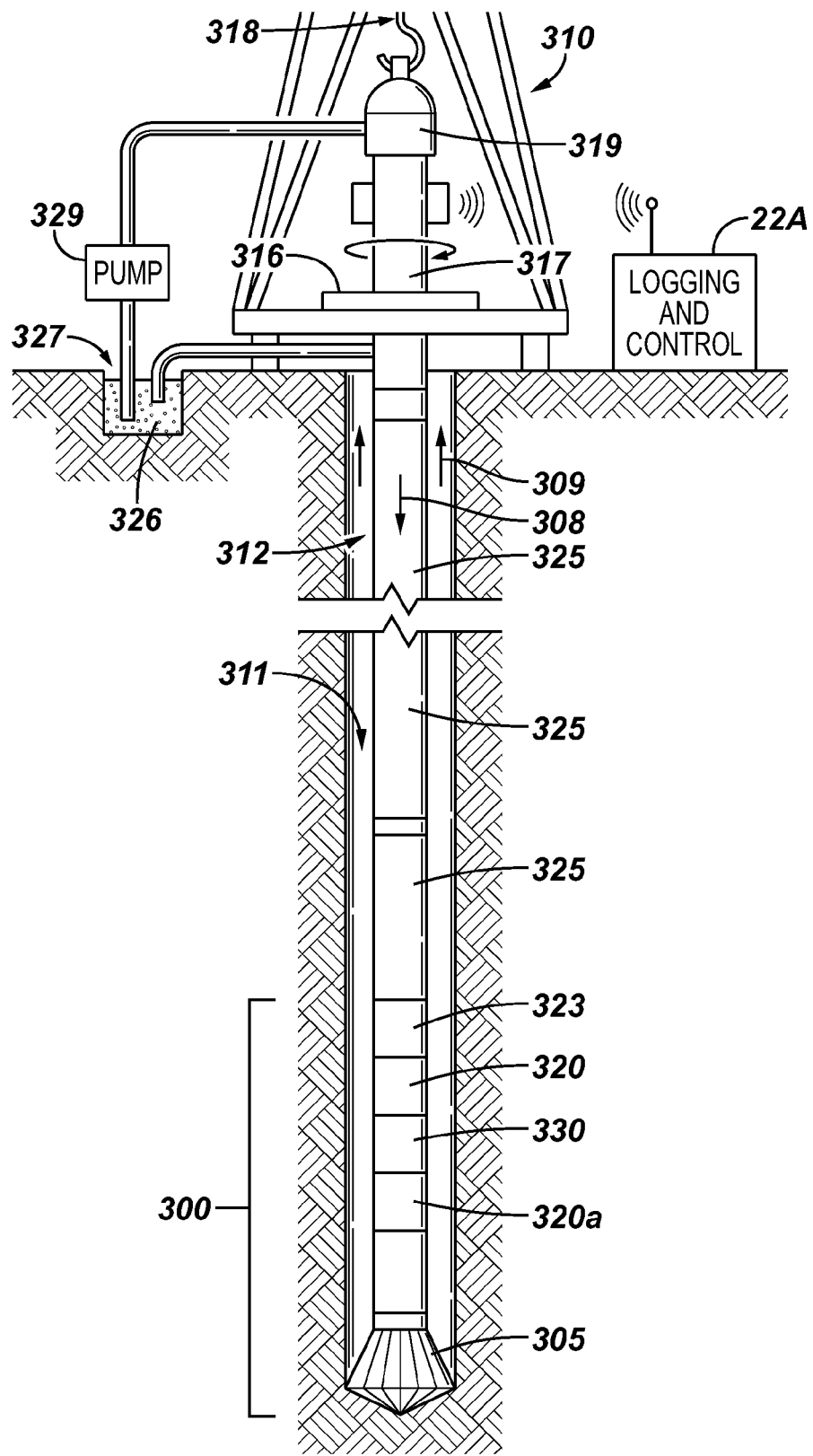
FIG. 1B shows a logging while drilling NMR instrument deployed in a wellbore.

FIG. 1B illustrates a wellsite system in which an NMR well logging instrument can be conveyed using a drill string or other pipe string for measurement during the drilling of the wellbore, or during other pipe string operations associated with the construction of a wellbore such as circulating and "tripping." The wellsite can be onshore or offshore. In the example system of FIG. 1B, a wellbore 311 is drilled through subsurface formations by rotary drilling in a manner that is well known in the art. Other examples of NMR instruments applicable to the present invention can be used in connection with directional drilling apparatus and methods. Accordingly, the configuration shown in FIG. 1B is only intended to illustrate a possible source of NMR measurements and is not intended to limit the scope of the present invention.

A drill string 312 is suspended within the wellbore 311 and includes a bottom hole assembly ("BHA") 300 proximate the lower end thereof. The BHA 300 includes a drill bit 305 at its lower end. The surface portion of the wellsite system includes a platform and derrick assembly 310 positioned over the wellbore 311, the assembly 310 including a rotary table 316, kelly 317, hook 318 and rotary swivel 319. The drill string 312 is rotated by the rotary table 316, which is itself operated by well known means not shown in the drawing. The rotary table 316 engages the kelly 317 at the upper end of the drill string 312. The drill string 312 is suspended from the hook 318. The hook 318 is attached to a traveling block (also not shown), through the kelly 317 and the rotary swivel 319 which permits rotation of the drill string 312 relative to the hook 318. As is well known, a top drive system (not shown) could alternatively be used instead of the kelly 317 and rotary table 316 to rotate the drill string 312 from the surface. The drill string 312 may be assembled from a plurality of segments 325 of pipe and/or collars threadedly joined end to end.

In one example, the BHA may include an instrument known as a dipole shear sonic imager ("DSI"). See the Uniform Resource Locator http://www.slb.com/services/evaluation/wireline_open_hole/petrophysics/acoustic_wireline-_tools/dipole_shear_sonic imager.aspx. Measurements from the DSI instrument may be used to estimate a formation parameter called surface relaxivity as will be explained further below. The DSI instrument may also be conveyed through the wellbore by any other means known in the art, for example the wireline conveyance shown in FIG. 1A.

In the present example, the surface system further includes drilling fluid ("mud") 326 stored in a tank or pit 327 formed at the wellsite. A pump 329 delivers the drilling fluid 326 to the interior of the drill string 312 via a port in the swivel 319, causing the drilling fluid 326 to flow downwardly through the drill string 312 as indicated by the directional arrow 308. The drilling fluid 326 exits the drill string 312 via water courses, or nozzles ("jets") in the drill bit 305, and then circulates upwardly through the annulus region between the outside of the drill string and the wall of the borehole, as indicated by the directional arrows 309. In this well known manner, the drilling fluid 326 lubricates the drill bit 305 and carries formation cuttings up to the surface, whereupon the drilling fluid 326 is cleaned and returned to the pit 327 for recirculation.

The bottom hole assembly 300 of the illustrated example can include a logging-while-drilling (LWD) module 320, a measuring-while-drilling (MWD) module 330, a steerable directional drilling system such as a rotary steerable system and/or an hydraulically operated motor such as a steerable motor, and the drill bit 305.

The LWD module 320 is housed in a special type of drill collar, as is known in the art, and can contain one or a plurality of known types of well logging instruments. It will also be understood that more than one LWD and/or MWD module can be used, e.g. as represented at 320A. (References, throughout, to a module at the position of LWD module 320 can alternatively mean a module at the position of MWD module 320A as well.) The LWD module 320A typically includes capabilities for measuring, processing, and storing information, as well as for communicating with the surface equipment. In the present embodiment, the LWD module 320 includes an NMR measuring instrument. An example configuration of such instrument is explained above with reference to FIG. 1A.

The MWD module 330 is also housed in a special type of drill collar, as is known in the art, and can contain one or more devices for measuring characteristics of the drill string and drill bit. The MWD module 330 further includes an apparatus (not shown) for generating electrical power for the downhole portion of the wellsite system. Such apparatus typically includes a turbine generator powered by the flow of the drilling fluid 326, it being understood that other power and/or battery systems may be used while remaining within the scope of the present invention. In the present example, the MWD 330 module can include one or more of the following types of measuring devices: a weight-on-bit measuring device, a torque measuring device, a vibration measuring device, a shock measuring device, a stick slip measuring device, a direction measuring device, and an inclination measuring device.

The foregoing examples of wireline and drill string conveyance of a well logging instrument are not to be construed as a limitation on the types of conveyance that may be used for the well logging instrument. Any other conveyance known in the art may be used, including without limitation, slickline (solid wire cable), coiled tubing, well tractor and production tubing.

A recording unit 22A may be disposed at the surface and may include data acquisition, recording, input, control and display devices similar to those of the recording unit shown at 22 in FIG. 1A.

In an example method according to the invention, measurements of nuclear magnetic resonance ("NMR") properties of subsurface formations may be made at one or more lateral depths into the formations adjacent to the wellbore. A NMR instrument, as explained above with reference to FIGS. 1A and 1B, can be moved along a wellbore drilled through subsurface formations. As explained with reference to FIG. 1A, NMR measurement made by the instrument includes prepolarizing nuclei in the formations by imparting a static magnetic field in the formations. The static magnetic field has known spatial amplitude distribution and known spatial gradient distribution. NMR phenomena are excited in the formations by applying a radio frequency ("RF") magnetic field to the prepolarized nuclei. A frequency of the RF magnetic field is selected to excite NMR phenomena in selected types of nuclei and within particular volumes in the formations ("sensitive volumes"). As is known in the art, the spatial position of the sensitive volume depends on the spatial distribution of the amplitude of the static magnetic field, the gyromagnetic ratio of the selected nuclei and the frequency of the RF magnetic field. Electromagnetic fields resulting from the induced NMR phenomena are detected and analyzed to determine NMR properties of the formations within the sensitive volumes. Such properties may include distribution of longitudinal and transverse relaxation times and distributions thereof ($T_1$ and $T_2$, respectively) and diffusion constants (D) of the various components of the formations. The foregoing parameters may be used to estimate, as non limiting examples, the total fractional volume of pore space ("total porosity") of the various subsurface formations, the bulk volume of "bound" water (water that is chemically or otherwise bound to the formation rock grains, such as by capillary pressure, and is therefore immobile), the fractional volume of the pore space occupied by movable water ("free water") and the fractional volume of the pore space occupied by oil and/or gas. As will be further explained below, the same NMR parameters may be used according to the present invention to estimate particle size distribution ("PSD") of certain subsurface rock formations, as well as a parameter known as surface relaxivity.

In one example, NMR measurements may be made using an instrument identified by the trademark MR SCANNER, which is a trademark of the assignee the present invention. In another example, the NMR measurements may be made using an instrument identified by the trademark CMR, which is also a mark of the assignee of the present invention. The NMR instrument, irrespective of type, is generally moved longitudinally along the wellbore and a record with respect to depth in the wellbore is made of the NMR properties of the various formations. The foregoing identified MR SCANNER instrument, in particular, can make measurements of NMR properties of the formations at a plurality of different, defined lateral depths of investigation. The lateral depths of investigation for the foregoing instrument are about 1.5 inches (3.8 cm), 2.7 inches (6.9 cm) and 4 inches (10.2 cm) from the wall of the wellbore. As explained above, the lateral depth of investigation of any particular NMR measurement is defined by the spatial distribution of the amplitude of the static magnetic field and the frequency of the RF magnetic field used to excite NMR phenomena. The example instruments described herein are not limitations on the scope of this invention but are provided only to illustrate the principle of the invention.

In general, according to the invention, NMR relaxometry measurements are made of the formation in order to determine, with respect to time, transverse spin echo amplitudes of the formation from initial transverse reorientation of the magnetic spins of susceptible nuclei in the formation (typically hydrogen associated with water) or longitudinal inversion recovery. It is generally understood that the rate of decay of spin echo amplitudes is a multiexponential function related to the quantity of and specific (intrinsic) relaxation time of various materials in the rock formation. In the case of a porous rock formation saturated with water, the relaxation time of the water will be related to both the relaxation time of the water and effects of water interacting by surface tension, among other mechanisms, with the surface of the rock grains. Thus, various size pores in a water saturated porous rock will exhibit intrinsic relaxation times related to the size of the pore spaces in the rock formation. The number of occurrences of pore spaces of particular sizes in a sample of the rock is known as the pore size distribution and as will be explained below, various techniques have been devised according to the invention to relate the pore space size distribution to the PSD.

One possible way to obtain PSD of formation comprised, for example, of sand particle from NMR measurements will now be explained. In a fully water saturated porous rock formation, NMR transverse relaxation time ($T_2$) measurements are related to the pore size of the rock formation through a property called surface relaxivity ($\rho_a$). The pore size of the rock is also related to the grain size of the rock. For uniform size rock grain particles and uniform packing of the grains, this relationship is given by the expression:

$$\frac{1}{\rho_2 T_2} = \frac{S}{V} = \frac{3(1-\phi)}{\phi r_g} \quad \text{(Eq. 1)}$$

where $\rho_2$ represents the surface relaxivity (in units of length per unit time $LT^{-1}$), $T_2$ represents the NMR transverse relaxation time (in units of time T), S represents the surface area ($L^2$), V represents the total pore volume ($L^3$) $\phi$ represents the porosity (the fractional volume of rock pore spaces with respect to total rock volume) and $r_g$ represents the rock grain radius (in units of length L).

While the present example, and additional examples to be explained below, use the transverse magnetic relaxation time ($T_2$), it should be clearly understood that techniques are known in the art for using NMR measurements to determine longitudinal relaxation time ($T_1$), and relationships are known in the art that relate $T_1$ to $T_2$ given the knowledge of certain rock formation and pore fluid parameters. Accordingly, the invention is not limited in scope to using $T_2$ measurements. In fact, the entire methodology outlined below carries over to $T_1$ measurements with the simple replacement of the subscript 2 with 1 in all the $T_2$'s and $\rho_2$'s, where $\rho_1$ is the longitudinal surface relaxivity, just as $\rho_2$ represents the transverse surface relaxivity. Both $T_1$ and $T_2$ contain similar information as far as this invention is concerned (even in combination with diffusion as discussed below for the case of $T_2$) and both can be used to extract grain size distributions as described for the $T_2$ case below.

Figure 2A:
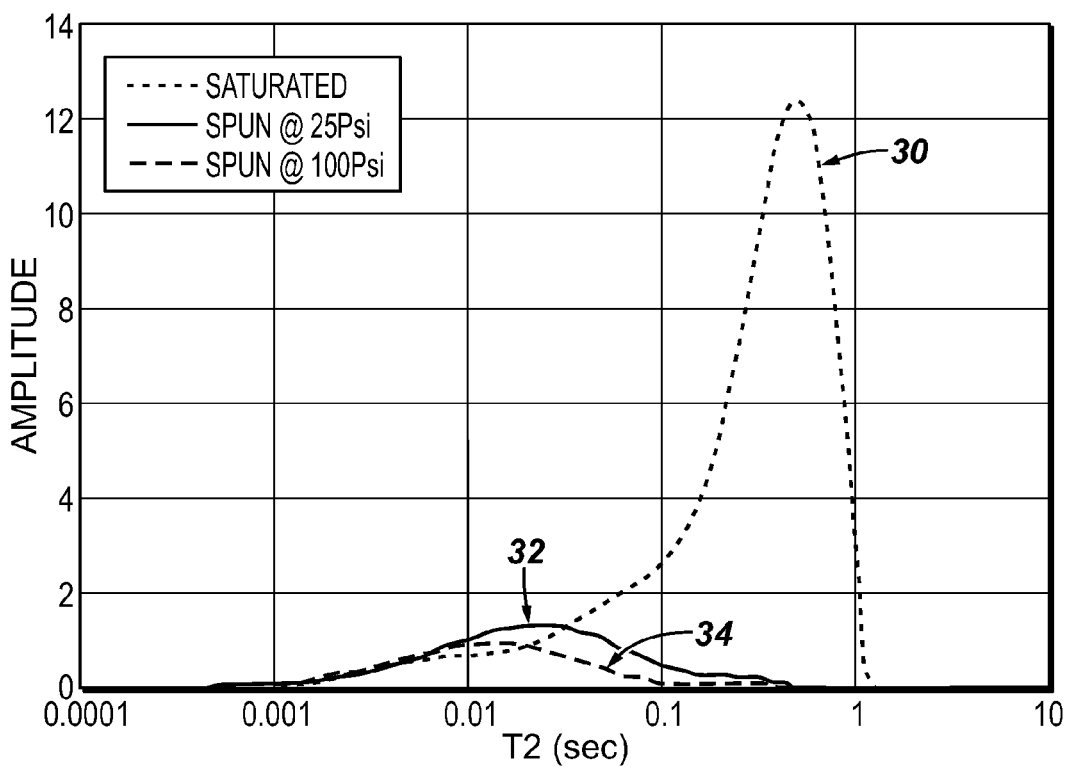
FIGS. 2A-2B show graphs of NMR relaxation time distribution with respect to grain size and cumulative grain size, respectively for a selected rock formation.
Figure 2B:
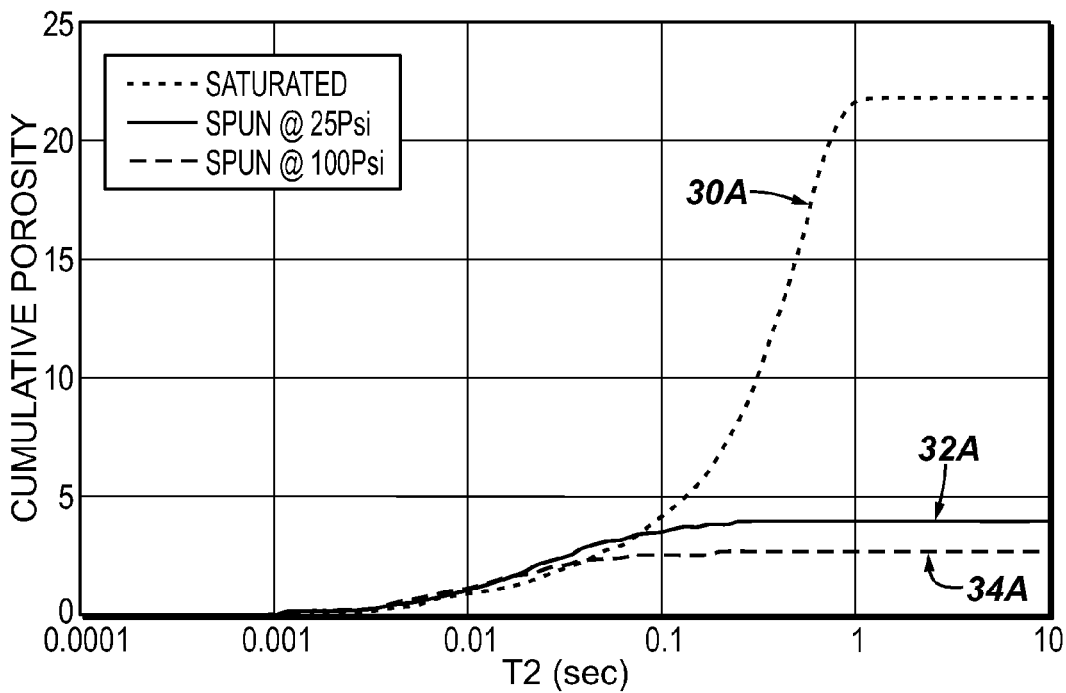
Figure 2C:
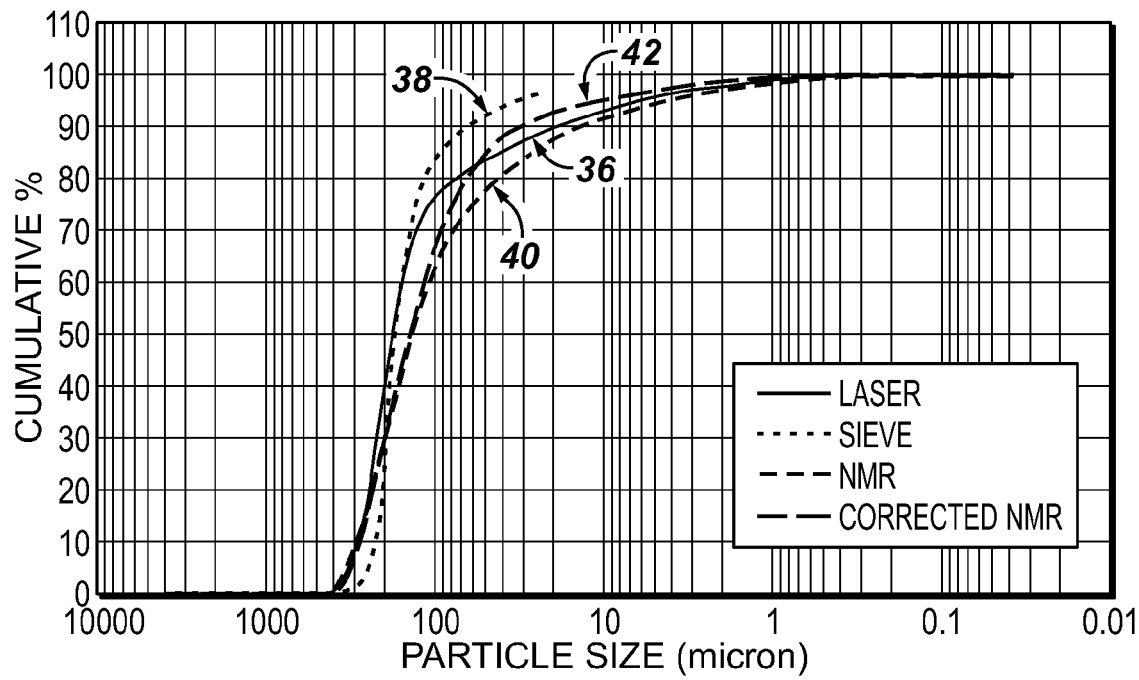
FIG. 2C shows a comparison of uncorrected NMR grain size distribution, corrected NMR grain size distribution, laser determined grain size distribution and sieve determined grain size distribution for the formation shown in FIGS. 2A and 2B.
Figure 3A:
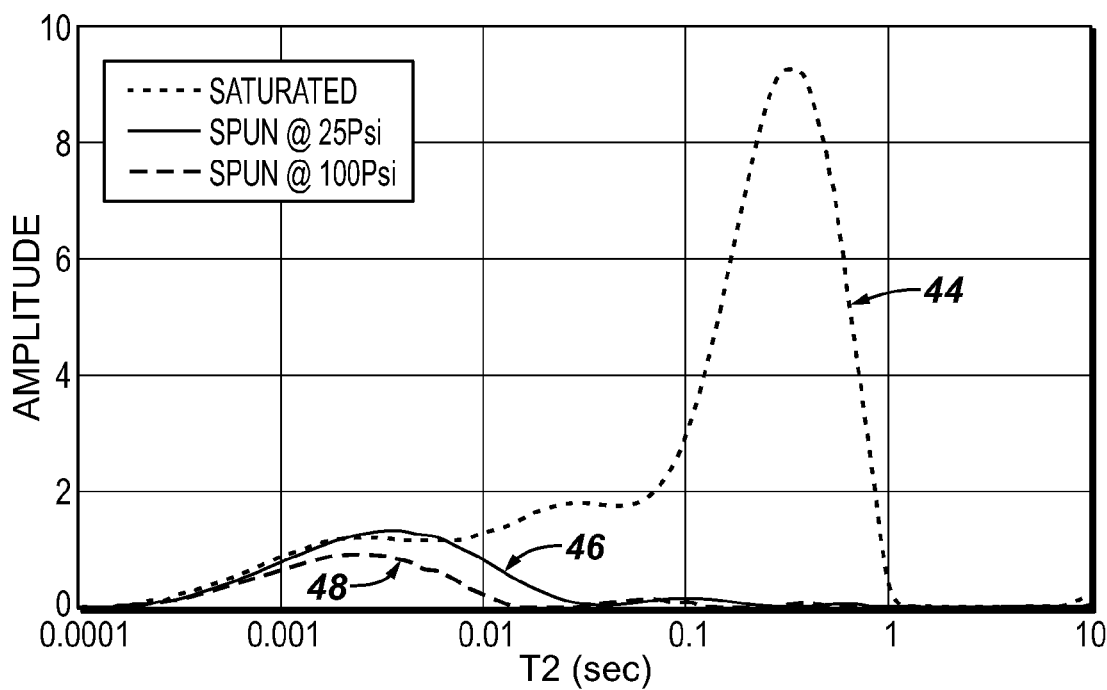
FIGS. 3A-3B show graphs of NMR relaxation time distribution with respect to grain size and cumulative grain size, respectively for a selected rock formation.
Figure 3B:
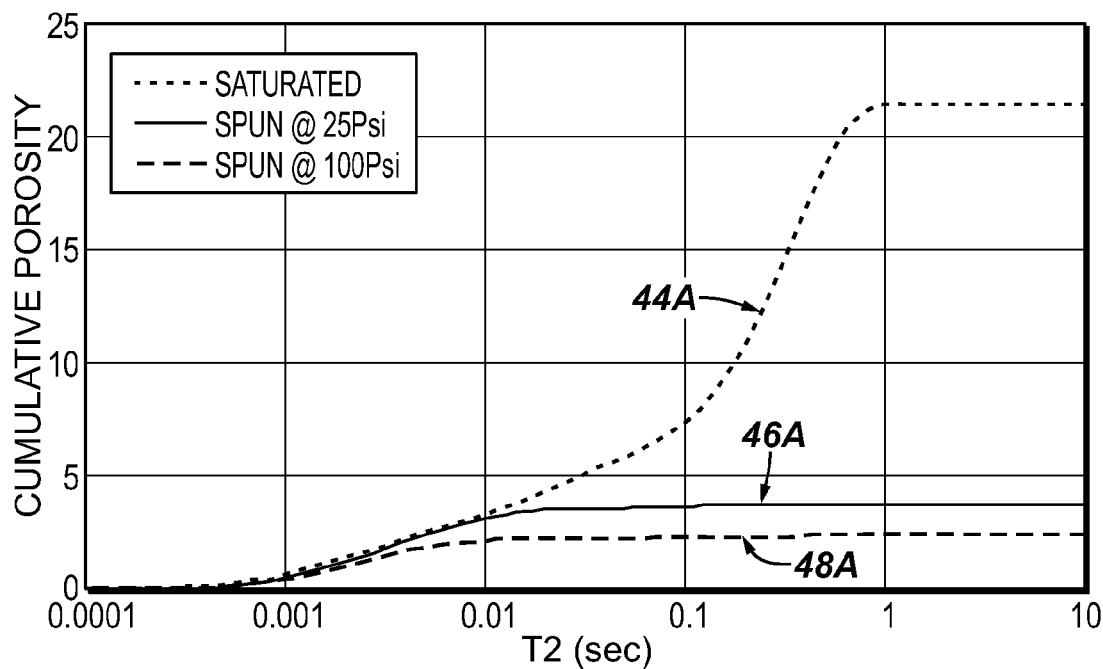
Figure 3C:
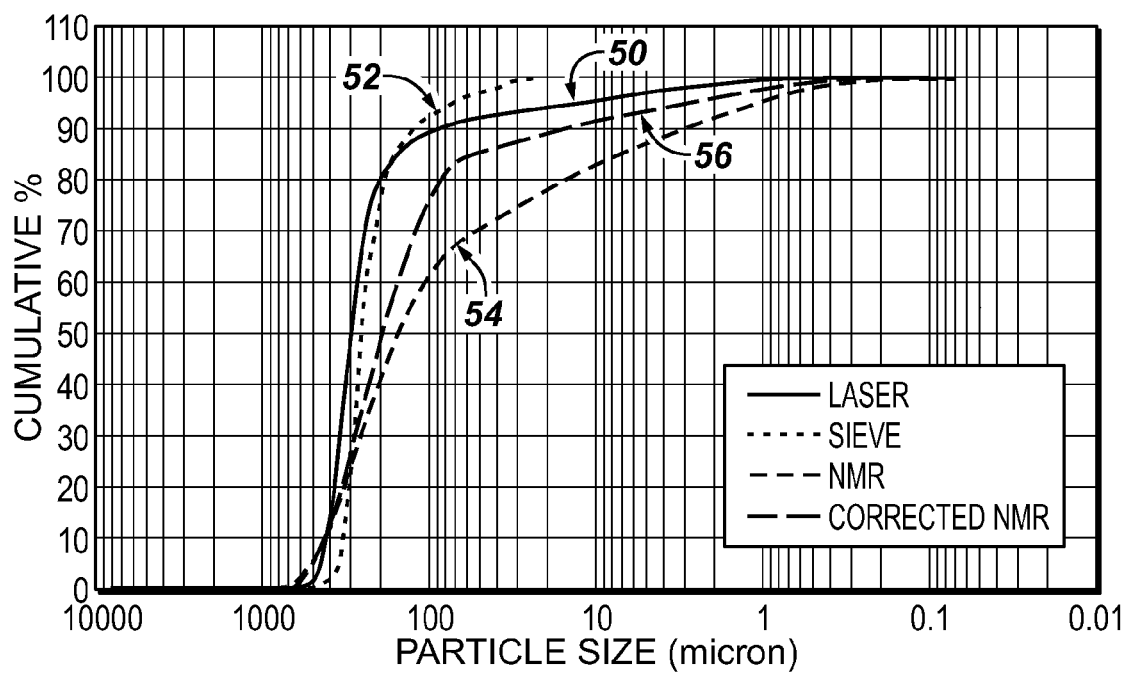
FIG. 3C shows a comparison of uncorrected NMR grain size distribution, corrected NMR grain size distribution, laser determined grain size distribution and sieve determined grain size distribution for the formation shown in FIGS. 3A and 3B.
Figure 4A:
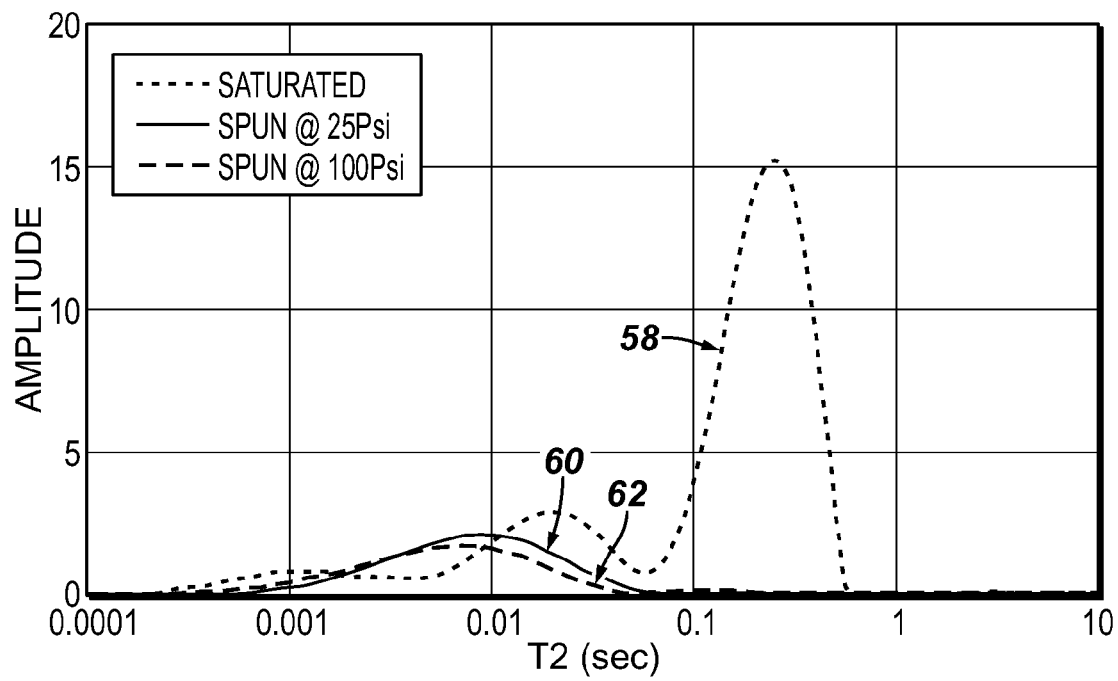
FIGS. 4A-4B show graphs of NMR relaxation time distribution with respect to grain size and cumulative grain size, respectively for a selected rock formation.
Figure 4B:
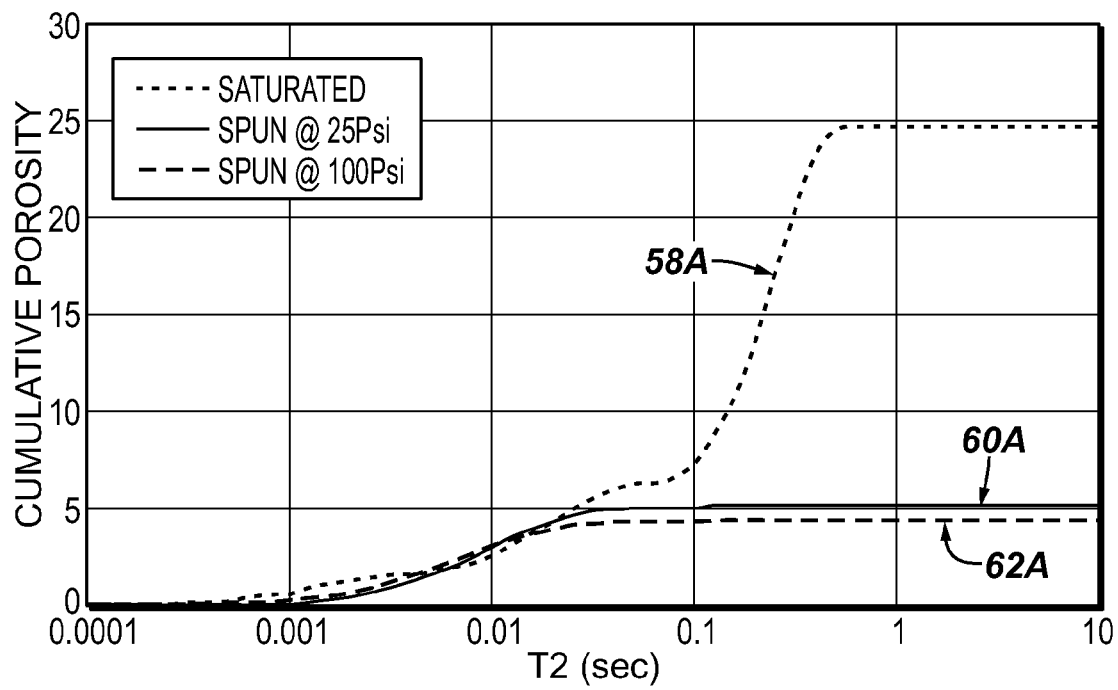
Figure 4C:
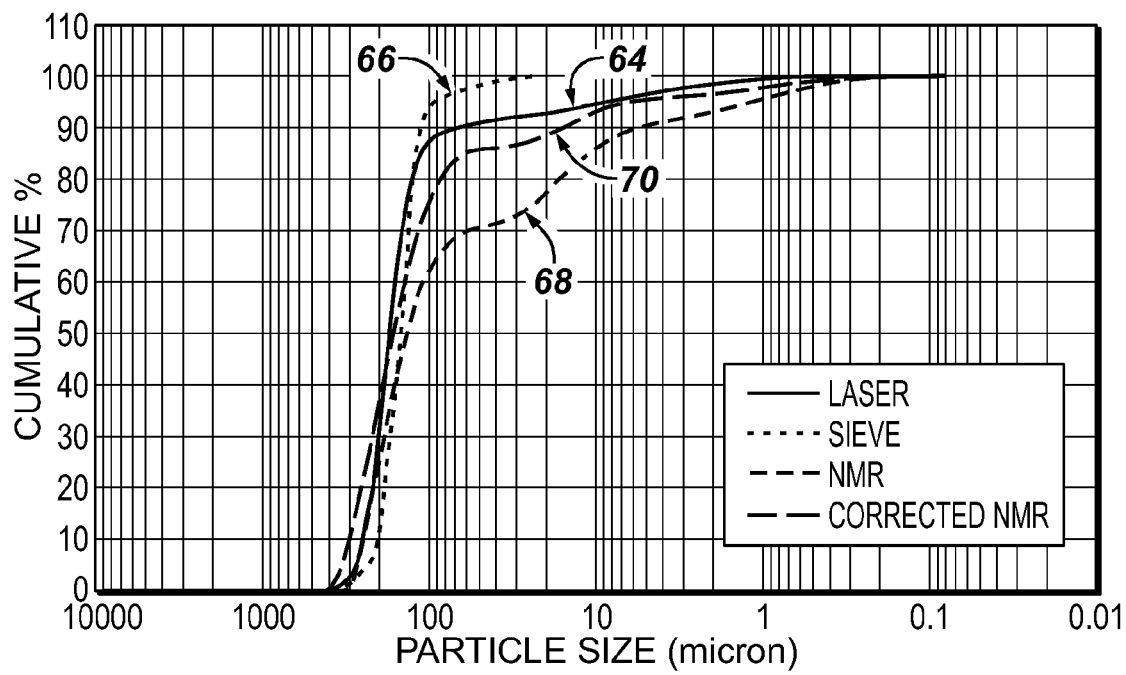
FIG. 4C shows a comparison of uncorrected NMR grain size distribution, corrected NMR grain size distribution, laser determined grain size distribution and sieve determined grain size distribution for the formation shown in FIGS. 4A and 4B.

In one example, a core sample, e.g., a whole drilled core, of particular subsurface rock formation may have the foregoing NMR $T_2$ measurements obtained. The PSD may be determined, for example, from sieve analysis or laser analysis. It is then possible to back calculate the surface relaxivity $\rho_2$ such that PSD predicted from NMR measurements, matches the PSD obtained from laser analysis or sieve analysis. The foregoing procedure was performed for seven different rock formation cores, and the results for three of the cores relevant to this description are shown in FIGS. 2A-2C for Berea sandstone, FIGS. 3A-3C for Briar Hill formation, and FIGS. 4A-4C for Castlegate formation. In FIG. 2A the transverse relaxation time ($T_2$) distribution is shown for water saturated rock at curve 30, for rock spun at 25 psi at curve 32 and spun at 100 psi at curve 34. Corresponding curves are shown in FIG. 2B at 30A, 32A, 34A. FIG. 2C shows curves for cumulative particle size distribution for PDS determined by laser, curve 36, sieve, curve 38, NMR uncorrected for surface relaxivity at curve 40 and NMR corrected for surface relaxivity at curve 42. Corresponding curves to those of FIG. 2A are shown at 44, 46 and 48 in FIG. 3A, at 44A, 46A, and 48A in FIG. 3B and at 50, 52, 54, 56 in FIG. 3C, respectively. Similarly, corresponding curves to those in FIG. 2A are shown in FIG. 4A at 58, 60 and 62, and in FIG. 4B at 58A, 60A, 62A, respectively. Corresponding curves to those in FIG. 2C are shown in FIG. 4C at 64, 66, 68 and 70, respectively.

As described above with reference to Eq. 1, the NMR $T_2$ is proportional to the surface-to-volume ratio (SVR) of the pore system. The SVR is further related to the grain size and the porosity, e.g., Eq. 1 for spherical rock grains. To account for non-spherical rock grains, a parameter A can be introduced to modify equation 1:

$$r_g = A\frac{3(1-\phi)\rho_2 T_2}{\phi} \quad \text{(Eq. 2)}$$

A=1 for spherical grains, and $r_g$ may be considered as some average of the grain dimensions (e.g., average of the long and short axis lengths). In practice, $\rho_2$=A$\rho_2$ may be used as an effective surface relaxivity parameter to be calibrated by experiment (e.g., laser or sieve measurements on rock samples).

For a rock formation that constitutes a packing of substantially single size grains, for example, a loose pack of glass beads, Fontainbleu sandstone, Bentheimer sandstone, the NMR $T_2$ distributions tend to show a narrow peak indicating the narrow range of pore sizes, and correspondingly, a narrow range of rock grain size. The $T_2$ distribution can be integrated to obtain the cumulative pore size distribution. Using equation 2, the $T_2$ (coordinate) axis of a graph of relaxation time with respect to frequency of occurrence or cumulative occurrence of can be converted to grain diameter (or radius) to plot the NMR derived PSD. The NMR derived PSD thus determined can be directly compared with the PSD obtained from laser and sieve measurements. Using the comparison of the NMR results and PSD (from laser or sieve analysis), the parameter $\rho_2$ can be empirically determined for particular formations.

For a rock formation with a mixture of different grain sizes, there are two different sets of conditions to consider in analysis of PSD using NMR measurements. The first set of conditions is that the different sized grains are spatially separated within different parts of the sample, such as may result from different deposition beddings. In such case, large grains will form larger pores and longer $T_2$, while the smaller grains will form smaller pores in separate parts of the formation. The $T_2$ distribution will still directly provide the grain size distributions (depending on determination of surface relaxivity as explained above).

In the second set of conditions, smaller grains may be disposed within the large pores formed by the larger grains. In such cases typically the smaller grains are much smaller than the larger ones, e.g., at least an order of magnitude difference in grain size. The small grains will form small pores with pore size and $T_2$ related their grain size (as may be represented by Eq. 1 or 2). Furthermore, because the small grains and corresponding pores occupy the pore space created by the large grains, the measured porosity within the large pores will be reduced. As a result, the $T_2$ distribution will show less signal from the large pores. In order to obtain the true grain volume of the large grains in such cases, the following procedure can be used.

In such rocks with a large range of pore sizes and sand grain sizes, $T_2$ distribution is often very broad with large pores at long $T_2$ and small pores at short $T_2$. Let the small pore volume be represented by $V_{sp}$, so that the total volume of the aggregates of the small grains will be $V_{sp}/\phi$, where $\phi$ is the porosity. The foregoing volume is assumed to be the missing pore volume that is originally created by the large grains. Therefore, the presence of the small pores contributes to an additional grain volume of the larger grains by a factor $V_{sp}(1-\phi)/\phi^2$.

The procedure to obtain a corrected grain size distribution is the following: First obtain NMR $T_2$ distribution by measurements made of the particular rock formation. Next, identify the large pores and correspondingly the large grains from the $T_2$ distribution. Frequently, this value is the peak amplitude at large values of $T_2$. Then assign a cut-off value, $T_{2c}$. For $T_2 > T_{2c}$, the values of $T_2$ are assigned to large grains; when $T_2 < T_{2c}$, the relaxation time is assigned to small grains. Then, integrate the $T_2$ distribution for the smaller grains (pores) to obtain the small grain/pore porosity $\phi_{sp}$. Then integrate the $T_2$ distribution for the large grains (pores) to obtain the large grain/pore porosity $\phi_{lp}$. The calculate the value $\phi_{sp}/(\phi\phi_{lp})+1$.

Multiply the foregoing value by the large pore part of the $T_2$ distribution (above the cutoff) to obtain a corrected large pore $T_2$ distribution. This corrected $T_2$ distribution contains both the short $T_2$ part and the long $T_2$ part. The corrected $T_2$ distribution may then be used as explained above to obtain the PSD.

The foregoing method using corrected NMR $T_2$ distribution will enhance the distribution determination for the larger grains and reduce the relative amount the smaller grains. For a rock formation having partial grain size mixing, i.e., some small grains are inside the large pores and some other smaller grains are spatially separated from the large grains, the true PSD will typically be between the two NMR derived PSDs as explained above (i.e., the uncorrected $T_2$ distribution method of Eq. 2 and the corrected method described above).

Figure 5:
FIG. 5 shows an empirically determined relationship between surface relaxivity and unconfined compressive strength.

Through experimentation, it has been determined that there is a correlation between the unconfined compressive strength ("UCS") of a rock formation and the value of surface relaxivity $\rho_2$ for the rock formation. An example of such relationship is shown in FIG. 5 at curve 72. The value of UCS for the rock formation may be obtained using measurements from, for example, the DSI instrument (e.g., 323 in FIG. 1B) or another acoustic instrument that enables determination of at least compressional velocity of the rock formations. The values of UCS may be converted using the relationship shown graphically in FIG. 5 to determine the surface reflexivity. The surface reflexivity so determined may be used with Eq. 1 to determine the PSD from the relaxation time distribution obtained from the NMR measurements. Examples of determining UCS of rock formations from measured acoustic properties is described in, C. Chang et al., Empirical relations between rock strength and physical properties in sedimentary rocks, Journal of Petroleum Science and Engineering 51 (2006) 223-237.

It has also been determined that it is possible to obtain values of the surface reflexivity for certain rock formations using both the transverse relaxation time distribution and the diffusion constant measured in a wellbore using a suitable NMR well logging instrument. Such technique may eliminate the need to calibrate the NMR determined distribution with respect to an actual rock sample or to make separate measurements to determine UCS. In a water-saturated sand pack (or any other porous medium), diffusing water molecules undergo frequent collisions with the grain surfaces. This leads to the effect of restricted diffusion, whereby the mean squared displacement of the NMR-active molecules (referred to as the spins) is reduced from the Einstein relationship for bulk diffusion:

$$\langle |\vec{r}(T_d) - \vec{e}(0)|^2 \rangle_{unrestricted} = 6 D_0 T_d \quad \text{(Eq. 3)}$$

where $T_d$ is the time during which the diffusion takes place. It is well-known that this effect can be described by a time-dependent diffusion coefficient $D(T_d)$ that is reduced from the molecular diffusion coefficient $D_0$. This reduction increases with the diffusion time $T_d$. At short times, the reduction only depends on the local surface-to-volume ratio of the pore, $S/V_p$:

$$\frac{D(T_d)}{D_0} = 1 - \frac{4\sqrt{D_0 T_d}}{9\sqrt{\pi}} \frac{S}{V_p} \quad \text{(Eq. 4)}$$

At the same time, wall collisions induce surface relaxation of the total magnetization which has been found to be typically given by exponential decay with a relaxation rate $$\frac{1}{T_{2,s}} = \rho_2 \frac{S}{V_p} \quad \text{(Eq. 5)}$$

The proportionality factor $\rho_2$ is the surface relaxivity. Combining Eqs. 4 and 5, one obtains for the short-time, or equivalently, large-pore regime:

$$\frac{D(T_2)}{D_0} = 1 - \frac{4\sqrt{D_0 T_d}}{9\sqrt{\pi}} \frac{1}{\rho_2} \frac{1}{T_{2,s}} \quad \text{(Eq. 6)}$$

Thus, with a measurement of $D(T_2)$, it is then possible to determine the surface relaxivity of the rock formation. If the short-time/large-pore regime cannot be reached due to experimental constraints (for example, if all the pores are too small or the available magnetic field gradients are too weak), it may still be possible to fit $\rho_2$ from a model form of $D(T_2)$ obtained by the Padé approximation interpolation between the short-time/large-pore formula in Eq. 6 and a constant tortuosity value of $D(T_2) = D_\infty$ which holds for long-times/small pores as described in, P. N. Sen., *Time-dependent diffusion coefficient as a probe of geometry*, Concepts in Magnetic Resonance, 23A:1, (2004). The interpolated formula is:

$$D(T_2) = D_0 \left[ 1 - \gamma \frac{\alpha L_D + (L_D/L_M)^2}{\alpha L_D + (L_D/L_M)^2 + \gamma} \right] \quad \text{(Eq. 7)}$$

where $$\alpha = \frac{4}{9\sqrt{\pi}} \frac{1}{\rho_2 T_{2,s}}, \; L_D = \sqrt{D_0 T_d}, \; \gamma = 1 - \frac{D_\infty}{D_0}, \; \text{and } L_M$$

is a heterogeneity length scale of the medium, which is typically much greater than the diffusion length $L_D$.

Note that $D_0$ is the diffusion constant of the bulk fluid, which is a property of the fluid by itself and can be determined from laboratory measurements. It is also possible to obtain well-defined tables for the diffusion coefficient of the given fluid as a function of temperature, as is the case for water and simple oils. $D_\infty$ is a property of the fluid as well the rock and can be approximated as:

$$D_\infty = D_0 \phi^{m-1} \quad \text{(Eq. 8)}$$

where $\phi$ represents the rock porosity and m is the cementation exponent that appears in the well-known Archie water saturation equation. Then $\gamma$ in Eq. 7 can be written as $\gamma = 1 -$ $\phi^{m-1}$. Thus, by knowing $D_0$ for the given fluid and m for the given rock, $D(T_2)$ can be determined for different values of $\rho_2$ using the Padé interpolation given by Eq. 7.

Figure 6:
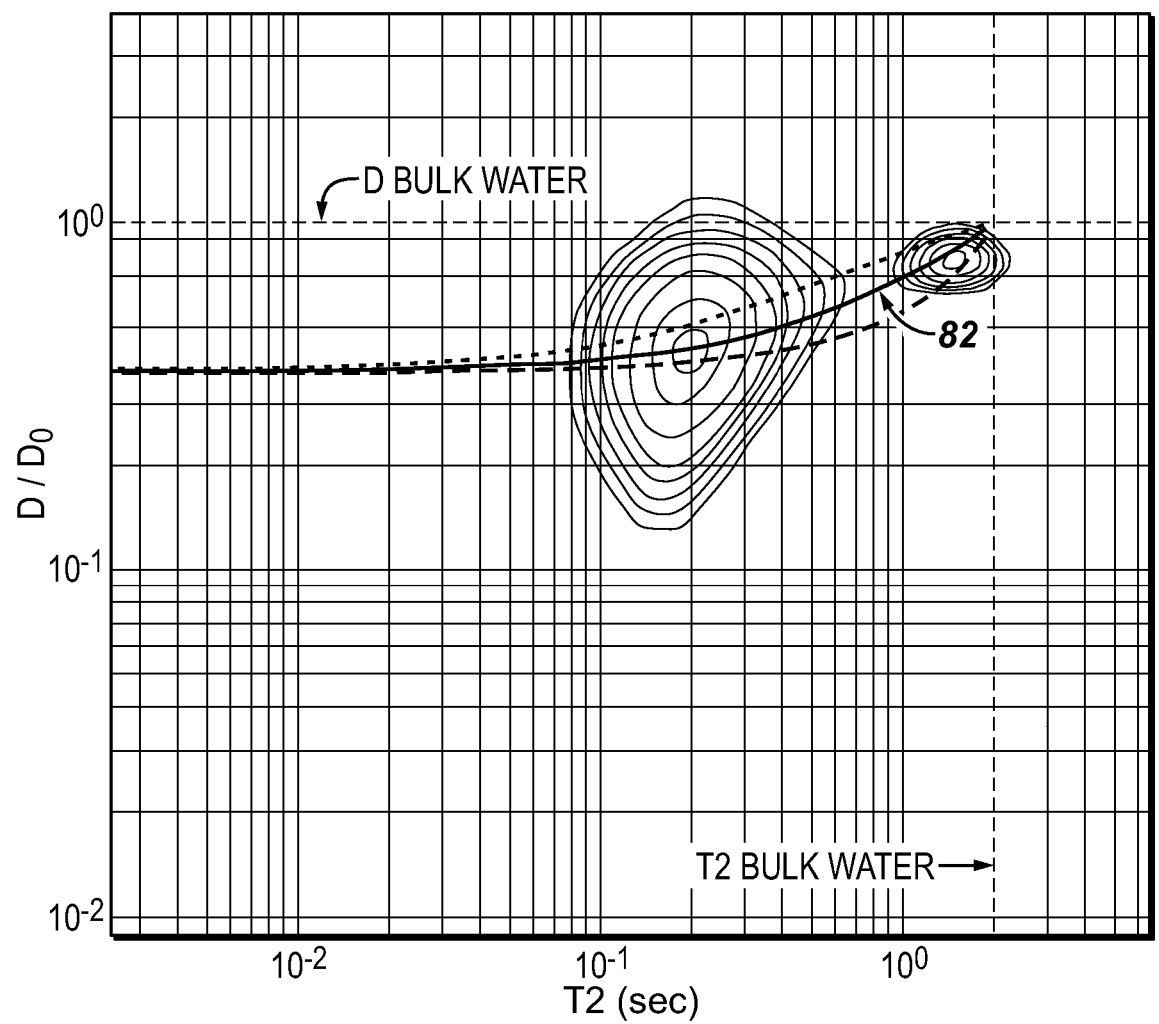
FIG. 6 shows an example of how the Padé form of $D(T_2)$ in Eq. 7 can be used to fit the surface relaxivity.

FIG. 6 shows an example of how the Padé form of $D(T_2)$ in Eq. 7 can be used to fit the surface relaxivity. The contour plot shows a diffusion-relaxation (DT2) map, which is a standard computed (answer) product delivered by oil services providers such as Schlumberger using their NMR logging instrument (e.g., one operated under the service mark MR SCANNER, which is a mark of the assignee of the present invention). The DT2 map is obtained by first encoding diffusion using either pulsed field gradients or constant magnetic field gradients via a spin echo or stimulated spin echo experiment—both of which are standard NMR pulse sequences—followed by a CPMG (Carr-Purcell-Meiboom-Gill) pulse sequence (also a standard NMR pulse sequence) to encode relaxation. The data acquired in this fashion is the inverted via a two-dimensional inverse Laplace transform to generate the DT2 map. The whole technique of acquiring such two-dimensional NMR methods is well documented and published in scientific literature. See, for example, Song et al, J. Magn. Reson. 154, 261-268 (2002); Hurlimann et al, J. Magn. Reson. 157, 31-42 (2002), U.S. Pat. Nos. 6,462,542 and 6,570,382). Similarly, one can acquire and process DT1 data, not shown here but also documented in the literature. The analysis for obtaining $\rho_1$ will be analogous to that for $\rho_2$ described in the following, except using the DT1 map in place of DT2. The curve that best matches the distribution, i.e., appears to go through the peak 82, in this example overplotted on the DT2 map corresponds to $\rho_2=2.5$ µm/s. Other criteria can be used to determine the best match to the distribution, such as a least-squares fit of the Padé curve to the mean or log-mean of the diffusion dimension of the distribution as a function of $T_2$.

Once the PSD has been determined, it may be used, as suggested in the Background section herein, to determine a parameter related to the completion of a wellbore, for example and without limitation, completion device type, completion screen opening or mesh size, or gravel size.

Methods according to the various aspects of the invention may enable determination of formation particle size distribution without the need to extract samples of the formation being evaluated. Necessary measurements to determine particle size distribution may be obtained from well log measurements.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining particle size distribution of a subsurface rock formation using measurements of at least one nuclear magnetic resonance property thereof made by moving a nuclear magnetic resonance well logging instrument along in interior of a wellbore penetrating the rock formation, comprising:
    in a computer determining a distribution of nuclear magnetic relaxation times from the measurements of the at least one nuclear magnetic resonance property;
    in the computer determining a surface relaxivity of the rock formation from a measurement of a formation parameter; and
    in the computer using the relaxation time distribution and the surface relaxivity to determine and display the particle size distribution.

2. The method of claim 1 wherein the formation parameter comprises a diffusion property of the rock formation.

3. The method of claim 2 wherein the diffusion property with respect to relaxation time is related to a molecular diffusion constant of a fluid disposed in pore spaces of the rock formation.

4. The method of claim 2 further comprising determining a Pade interpolated formulation of the diffusion property.

5. The method of claim 1 wherein the parameter comprises an acoustic property of the rock formation, wherein the acoustic property is used to determine an unconfined compressive strength of the rock formation, and an empirical relationship between the unconfined compressive strength and the relaxivity is used to determine the relaxivity.

6. The method of claim 1 wherein the parameter comprises particle size analysis of samples of the rock formation.

7. The method of claim 6 wherein the particle size analysis comprises particle size distribution, and wherein the relaxation time distribution is correlated to the analyzed particle size distribution.

8. The method of claim 1 wherein the nuclear magnetic relaxation times comprise transverse nuclear magnetic relaxation times.

9. The method of claim 1 wherein the nuclear magnetic relaxation times comprise longitudinal nuclear magnetic relaxation times.

10. The method of claim 1 further comprising in the computer separating the relaxation time distribution into a short time section and a long time section by selecting a cutoff time related to a selected separation between large rock grains and small rock grains.

11. The method of claim 1 wherein the particle size distribution is used to determine at least one parameter related to completion of the wellbore.

12. The method of claim 11 wherein the parameter comprises at least one of completion device type, completion screen opening or mesh size and gravel size.

13. A method for determining particle size distribution of a subsurface rock formation, comprising:
    moving a nuclear magnetic resonance well logging instrument along a wellbore drilled through the subsurface rock formation;
    measuring at least one nuclear magnetic resonance property of the rock formation using the instrument;
    in a computer determining a distribution of nuclear magnetic relaxation times from the measurements of the at least one nuclear magnetic resonance property;
    in the computer determining a surface relaxivity of the rock formation from a measurement of a formation parameter; and
    in the computer using the relaxation time distribution and the surface relaxivity to determine and display the particle size distribution.

14. The method of claim 13 wherein the parameter comprises a diffusion property of the rock formation made by the nuclear magnetic resonance instrument.

15. The method of claim 14 wherein the diffusion constant with respect to relaxation time is related to a molecular diffusion constant of a fluid disposed in pore spaces of the rock formation.

16. The method of claim 14 further comprising determining a Pade interpolated formulation of the diffusion property.

17. The method of claim 13 wherein the parameter comprises an acoustic property of the rock formation, wherein the acoustic property is used to determine an unconfined compressive strength of the rock formation, and an empirical relationship between the unconfined compressive strength and the relaxivity is used to determine the relaxivity.

18. The method of claim 13 wherein the parameter comprises particle size analysis of samples of the rock formation.

19. The method of claim 18 wherein the particle size analysis comprises particle size distribution, and wherein the relaxation time distribution is correlated to the analyzed particle size distribution.

20. The method of claim 13 wherein the nuclear magnetic relaxation times comprise transverse nuclear magnetic relaxation times.

21. The method of claim 13 wherein the nuclear magnetic relaxation times comprise longitudinal nuclear magnetic relaxation times.

22. The method of claim 13 further comprising in the computer separating the relaxation time distribution into a short time section and a long time section by selecting a cutoff time related to a selected separation between large rock grains and small rock grains.

23. The method of claim 13 wherein the moving the instrument comprises moving an armored electrical cable through the wellbore, the instrument disposed proximate one end of the cable.

24. The method of claim 13 wherein the moving the instrument comprises moving a pipe through the wellbore, the instrument coupled within the pipe.

25. The method of claim 13 wherein the particle size distribution is used to determine and display at least one parameter related to completion of the wellbore.

26. The method of claim 25 wherein the parameter related to completion comprises at least one of completion device type, completion screen opening or mesh size and gravel size.

* * * * *